United States Patent [19]

Sweeney

[11] 4,063,551
[45] Dec. 20, 1977

[54] BLOOD PULSE SENSOR AND READOUT

[75] Inventor: James Stevens Sweeney, Laguna Beach, Calif.

[73] Assignee: Unisen, Inc., Irvine, Calif.

[21] Appl. No.: 674,113

[22] Filed: Apr. 6, 1976

[51] Int. Cl.² ............................................. A61B 5/02
[52] U.S. Cl. ........................ 128/2.05 P; 128/2.05 T
[58] Field of Search ................... 128/2.05 R, 2.05 P, 128/2.05 T, 2.05 E, 2 C, 2.05

[56] References Cited

U.S. PATENT DOCUMENTS

| 3,040,737 | 6/1962 | Kompelien et al. | 128/2.05 E |
| 3,228,391 | 1/1966 | Fitter et al. | 128/2.05 T |
| 3,602,213 | 8/1971 | Howell et al. | 128/2.05 P X |
| 3,704,706 | 12/1972 | Falkner et al. | 128/2.05 T X |
| 3,769,974 | 11/1973 | Smart et al. | 128/2.05 P |
| 3,841,314 | 10/1974 | Page | 128/2.05 A |

Primary Examiner—Stephen C. Pellegrino
Attorney, Agent, or Firm—Thomas J. Plante

[57] ABSTRACT

A highly sensitive electronic blood pulse sensor and readout device is disclosed which is self-powered and can be mounted on the subject's wrist. The sensor portion has a plurality of light emitters which are arranged to emit pulsed infra-red light waves having a wavelength readily absorbed by blood constituents, and a plurality of light detectors highly responsive to the emitted wavelength. The level of detected illumination is used to control by feedback the level of emitted illumination, in order to compensate for variations in flesh translucency. A separate "noise" responsive sensor is used to counteract the noise-inducing tendencies of motion.

21 Claims, 7 Drawing Figures

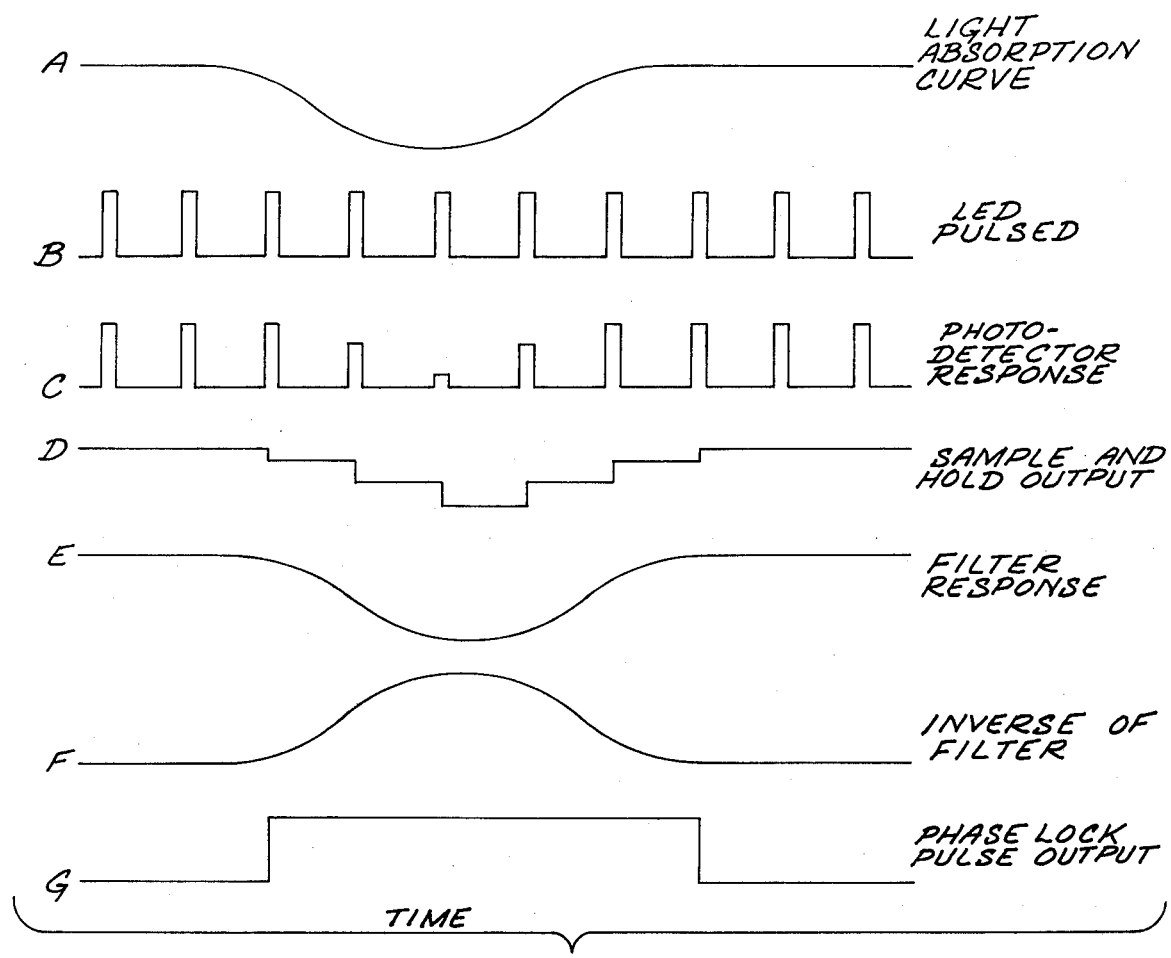
FIG. 5
FIG. 6
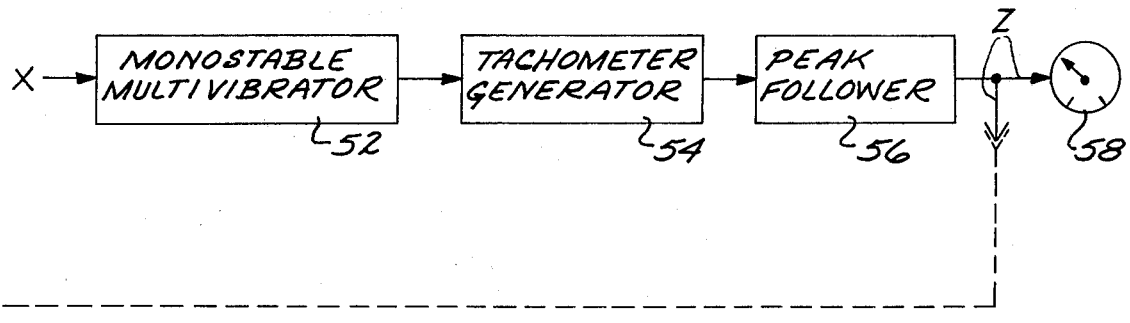
FIG. 7
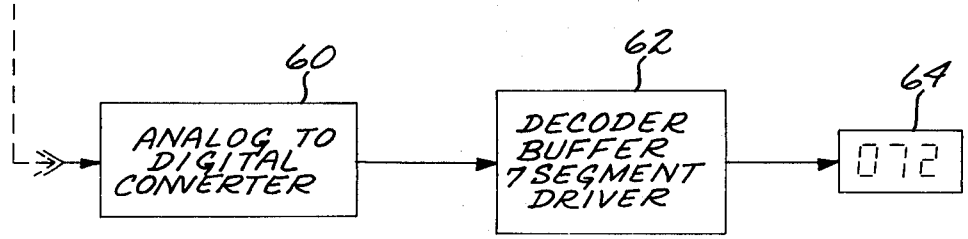

BLOOD PULSE SENSOR AND READOUT

BACKGROUND OF THE INVENTION

This invention relates to the field of blood pulse indicating devices, and is particularly concerned with the need for an easily portable, reasonably-priced, non-invasive device for sensing blood pulses and providing information concerning such vital matters as heart rate and blood pressure.

As indicated by the numerous patents in this field, there is a substantial requirement for an instrument which will measure these physiological conditions unobtrusively and accurately. In order to be easily portable and thus useful in monitoring heart reactions during active physical exertions of the patient, the instrument needs to be self-contained and self powered. The preferred, non-interfering position for mounting such an instrument is on the wrist of the patient; and its output preferably should be readable directly on the instrument.

Availability of a commercially satisfactory self-powered heart rate monitor having the attributes mentioned above would be of substantial use both in: (a) outpatient management, particularly in cases of cardiac dysfunction, and also in cases of pulmonary, systemic vascular, neural, and renal dysfunction; and (b) physical fitness training where a participant can obtain maximum benefit by functioning at an optimal heart rate level.

The following prior U.S. patents relating to this general field constitute all of the prior art known to applicant; they are the result of two novelty searches made relative to applicant's invention: U.S. Pat. Nos. Okada et al., B321,018; Norris, 3,631,849; Funfstuck et al., 3,675,643; Herczfeld et al., 3,704,706; Manuel et al., 3,742,937; Smart et al., 3,769,974; Stephens, 3,796,213; Orr et al., 3,807,388; Scheidt, 3,815,583; Raddi et al., 3,826,246; Manuel et al., 3,838,684; Page, 3,841,314; Gebben et al., 3,850,169; Dunegan, 3,871,362; Blick, 3,880,145; Wilcox, 3,881,466.

Of the listed patents, three seem to call for specific discussion herein. Smart U.S. Pat. No. 3,769,974 discloses a red light reflecting device which has "a plurality of light emitting diodes from which red light of a wavelength of from 6,000 to 9,000 angstroms is emitted." This light is reflected from an artery "to a sensor which varies as a function of variations in pulse pressure in the artery."

Herczfeld, Herczfeld and Klafter U.S. Pat. No. 3,704,706 discloses an "apparatus for detection of pulse rate . . . comprising a solid state probe . . . housed to direct light upon a patient's finger and a photodetector housed for receiving reflected light from such finger." The light source is a galium arsenide laser having a peak emission at 6,700 angstroms, in the red range of the color spectrum; and the photodetector is an NPN silicon device having high sensitivity through the frequency range of the emission spectrum of the laser.

Dunegan U.S. Pat. No. 3,871,362 discloses a pulse rate device using a phototransistor measuring device to indicate changes in reflection from the patient's finger during each heart beat.

It is applicant's opinion that the present invention provides for the first time a functionally and commercially practical solution of the general problems of pulse monitoring devices, a solution which is fundamentally different from, and radically more successful than, the prior devices in the field.

SUMMARY OF THE INVENTION

The present invention includes a plurality of significant new concepts which provide for the first time an instrument for measuring heart rate having high accuracy combined with a low power requirement. It can therefore be used as a self-powered, wrist-mounted device having either analog or digital readout.

This result is enhanced by combining several concepts, each of which appears to be unique in this field; so the claims will cover these concepts both individually and collectively. These concepts are:

1. Sensing the light absorption of infra-red light by the blood, which provides radically improved sensor efficiency as compared to the light-reflecting devices of the prior art;
2. Use of multiple light detectors to avoid undue position sensitivity of the device, and thus forestall signal errors or weakness due to position variations of the device on the wrist;
3. Combining each light detector with a separate light emitter in a physically paired relationship having the correct angular and distance values for high signal output;
4. Providing a servo, or feedback, means for compensating automatically for variations in the flesh translucency of different subjects;
5. Use of a separate sensor which answers only motion, and which permits a high signal-to-noise output ratio when the motion-induced noise signal is subtracted from the light detector signal;
6. Use of an intermittent, but fully accurate, sampling technique which radically reduces the power requirements of the device;
7. Use of an unusually simple conversion technique for providing digital read-out in pulses per minute; and
8. Use of a digital filtering technique to lower noise susceptibility in the digital readout device.

BRIEF DESCRIPTION OF THE DRAWINGS

FIG. 5 is a diagram comparing the electronic signals at various stages in the circuits shown in FIGS. 3 and 4.

FIG. 6 is a schematic block diagram of that portion of the circuit which differs from the circuit of FIG. 4 in an analog version of the heart rate monitor; and FIG. 7 is a schematic block diagram of that portion of the circuit which differs from the circuit of FIG. 4 in an analog-digital version of the heart rate monitor.

DETAILED DESCRIPTION OF SPECIFIC EMBODIMENTS

The general subject matter of my invention includes several novel concepts not heretofore applied to pulse measuring devices. An important new concept is the use of an infra-red light emitting and detecting system which has a frequency selected for maximum light absorption by the blood. In devices which have been built and demonstrated, I have found an infra-red wavelength of approximately 9300 angstroms to be highly satisfactory. This takes into account three major considerations: (a) receptor availability, (b) transmitter availability, and (c) the light absorption spectrum of oxygenated blood. Referring to "(a)", there are available efficient silicon phototransistors which have peak response at about 9300 angstroms. Referring to "(b)", use of these receptors tends to determine the needed wavelength characteristics of the emitters, which should closely match the characteristics of the receptors. The preferred emitters in this situation are galium arsenide light emitting diodes. Referring to "(c)", this wavelength (9300 angstroms) is within the absorption spectrum of the hydroxyl constituents of arterial blood.

Prior art devices have used measurements of light reflection to indicate blood pulse rates. My device measures light absorption by the blood, using a drop in back scatter to indicate increased absorption, which in turn indicates increased volume of flow. So the occurrence of each pulse is easily detected. The energy needed in a light absorption device of the type discussed herein is only about 1/1000 of the energy needed in the light reflecting devices of the prior art. So there is a reduction in power requirements which constitutes an efficiency improvement approximating 1,000 to 1 over prior devices. Obviously, this can constitute the difference between commercially feasible and non-feasible devices where a wrist-mounted pulse monitor is desired.

Figure 1:
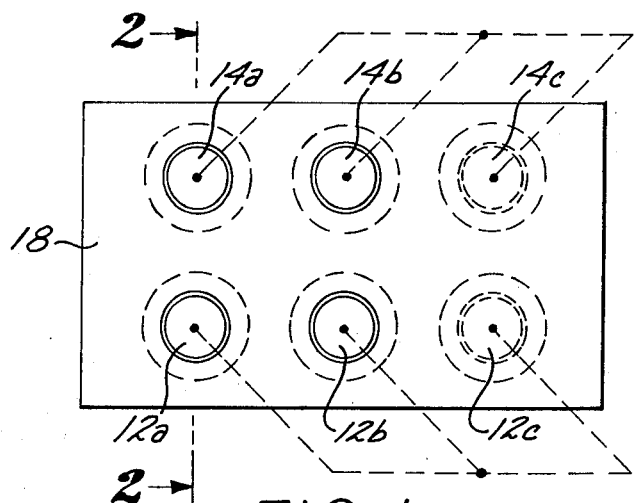
FIG. 1 is a plan view of the heart rate monitor structure and its light emitting and light detecting elements, taken from the underside of the device, which in operation would be held against the patient's wrist.
Figure 2:
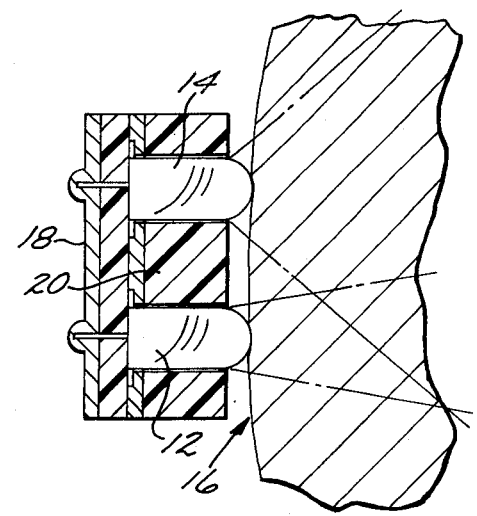
FIG. 2 is a cross sectional view taken on the line 2—2 of FIG. 1, showing the relationship of one pair of light emitting and detecting elements.

Referring now to the drawings, it will be observed that FIGS. 1 & 2 show a sensor comprising a plurality of light sources 12, and a plurality of light detectors 14, which are arranged in pairs 12a and 14a, 12b and 14b, etc., as shown in FIG. 1. There should be at least two such pairs; and the number of pairs can be increased to obtain decreased position sensitivity consistent with economic limitations. The sensor is shown mounted on the wrist, generally indicated by the numeral 16. The sensor, which may have a diameter of about one-half inch, is placed directly over the brachial artery.

FIG. 2 shows the bottom ends of the emitters 12 and detectors 14 pressing against the wrist 16. Since FIG. 1 shows the underside of the sensor unit, the wrist surface does not appear in that figure. FIGS. 1 & 2 are not intended to show circuit connections, but only a possible supporting arrangement for the sensor components. The light-detecting photocells 14, and the light-emitting diodes 12, are shown soldered to one side of a printed circuit board 18. There is, of course, no direct electrical connection between the light sources 12 and the detectors 14. A plastic cover 20 may be secured to the underside of the assembly which is supported on the patient's wrist.

As stated above, the light which enters detectors 14 does not measure the reflection of light by the artery, but instead the back scatter which remains after the absorption of light by the oxygenated blood in the artery and arterioles. Each light source 12 is an infra-red light emitting diode. As already indicated, a wavelength light in the neighborhood of 9300 angstroms has been used with eminent success. Clearly the concepts of this invention do not require this particular wavelength, but permit the use of any wavelength within the infra-red range in which blood constituents show a strong absorption band. Each light emitting diode 12 is a relatively efficient light source because it is essentially monochromatic and does not involve the waste of white light, which has a broad frequency spectrum.

The light detectors 14 are photocells which have high sensitivity to the wavelength emitted by the light sources 12. It is important that a plurality of photocells 14 be used. The prior art devices using a single light detecting device are very position sensitive, i.e., their placement with respect to the artery is critical because light detection efficiency is dependent on exact location. By utilizing a plurality of detectors, I am able to eliminate positioning problems, and insure effective functioning of the sensor in spite of reasonable variations in its location with respect to the artery.

After extensive experimenting, I have concluded that each light detector 14 should be physically paired with a light emitter 12, as is shown by the pairs 12a-14a, 12b-14b, 12n-14n. This is clearly the most effective means for obtaining a reliable and consistent sensor signal.

In FIG. 2, the dashed lines illustrate diagramatically the dispersion of infra-red rays emitted by the emitter 12a and received by the detector 14a. The angular dispersions of rays, respectively, of the emitter and detector should overlap optimally at a particular depth, in order to yield optimal illumination of the selected arterial system. A narrow angle of emission (such as 10°) may be used to illuminate the artery, and a broad angle (such as 90°) may be used to receive the light beam which has been modulated by absorption of light by the blood. There is a critical range of spacing between the emitter and detector elements 12a and 14a required to obtain the highest amplitude signal without saturating the photo detector. This spacing range depends in part on the dispersion angles of the elements. In the ideal situation, the spacing is in the approximate range of 0.25 to 0.35 in.

As stated above, using a multiplicity of paired photodetectors and emitters permits variability in the positioning of the sensor array over the artery, without loss of overall sensor effectiveness.

FIGS. 3 through 8 show the general functions of the circuitry which measures the pulse rate. An electrical pulse generator 24 is designed to create the electrical pulse rate which will periodically sample the blood flow measurement to provide precise information with the minimum expenditure of power. My electrical pulsing arrangement reduces the power requirements of the device, as compared to a continuous light source, by a ratio of nearly 1,000 to 1. So this power reduction, coupled with the power reduction obtained by measuring the blood absorption of infra-red light, provides a radical improvement in practicability of the portable heart rate indicator.

The electrical pulse rate of the pulse generator 24 should have a frequency of approximately 20 Hertz. This frequency should be at least double the highest frequency in the pulse wave form of the heartbeat, which is about 10 Hertz. This conforms to the assumed need for occurrence of a sampling electrical pulse at least twice per cycle. The advantages of minimizing power requirements dictate that the frequency used be at or near the low end of the range which will function properly.

Also the need for power reduction dictates that the pulse width be as small as possible consistent with the response characteristics of the photo detectors. The electrical pulse width currently being used in my heart rate monitors is 60 microseconds. Thus, the infra-red light is "turned on" 20 times per second for 60 microseconds each time. So it is on only 1200 microseconds per second, or 1/833 of the total time. The electrical current level needed during interrogation is in the vicinity of 3 milliamperes. So the reduction of average current to the ratio of 1/833 results in a need for current of only about 3.6 microamperes.

The electrical pulses from the pulse generator 24 pass through a driver, or power source, 26 for amplification, and develop light pulses from the light emitting diodes 12. The pulsed light is represented on line B of FIG. 5; line A of FIG. 5 represents the light absorption curve of the blood.

The light pulses are detected by the photocells 14. The intensity of light received by the photo detector array drops very significantly as the flow of blood in the artery increases. This is due to increased absorption of the infra-red light by the blood, such light absorption by the blood being a highly resonant phenomenon.

In order to provide a fully practical device, I have found it necessary to develop a means for compensating for person-to-person variations in the transparency of the flesh to infra-red light. Human flesh varies significantly in its transparency to infra-red light. Highly transparent flesh yields a very high level of illumination to the photo detector array, in many cases saturating the photo detector, and thereby reducing the detectability of the heart rate signal substantially.

To control this illumination level, a combined electronic servo and low pass filter 28 are used to: (1) sense the average illumination level at the photo detectors 14; and (2) control the current through the infra-red light emitting diodes 12, by varying the amplification effect of driver 26. As the average signal level from detectors 14 decreases, the amplification of driver 26 increases; and as the average signal level from detectors 14 increases, the amplification of driver 26 decreases. (The low pass filter removes heart rate signals from the average illumination signal to preclude signal degeneration.) In this manner, a constant illumination level at the photo detectors is obtained regardless of flesh transparency.

The back scatter light received by the photo detectors 14 is converted to electrical signals which are fed to preamplifier 34. The electrical output of preamplifier 34, which output is represented on line C of FIG. 5, consists of pulses having the same frequency as those of pulse generator 24, but proportional in amplitude to the amount of back scatter light. Therefore, the amplitude of the electrical pulses is reduced as the blood pulse occurs, increasing the absorption of the infra-red light. The waveform of the electrical pulse variations follows the general pattern of the light absorption curve of the blood represented on line A of FIG. 5; as the heart pulse occurs, the amplitude of measured back scatter light drops very significantly due to increased absorption of the infra-red light by the blood.

The sample and hold circuitry 36 changes the electrical signal output of the preamplifier 34 to the general form shown on line D of FIG. 5. And the smoothing filter 38 further converts the electrical output to the waveform shown on line E of FIG. 5, which is essentially a reconstruction of the waveform on line A. The waveform on lines E and A has the frequency of the heart pulse and also has an amplitude variation proportional to the amplitude variation in the heart pulse, but its shape is the inverse of the actual heart pulse waveform (pressure or volume) because the electrical signal amplitude decreases as blood flow increases.

The movement sensor 40 is used to generate a signal which indicates movement of the patient's wrist. As a movement sensor, I use a piezo resistive device which is designed to sense only movement. The same movement is also represented as noise in the signal received by the preamplifier 34. The movement signal of the movement sensor 40 and the signal from smoothing filter 38 are both fed to a differential amplifier 42, where the movement signal 40 is algebraicly subtracted from the heart-rate-plus-movement signal of the main sensor circuit, thereby causing a substantially noise-free signal output from the differential amplifier 42.

Most heart rate sensor systems are particularly subject to motion-induced "artifacts." Unfortunately, the motion-induced noise occupies about the same frequency band as the heart signal. Generally, however, its wave shape is quite different from the heart signal because the amplitude and period of motion-induced noise are random events. Subtraction of the signals caused by the motion-only sensor 40 from the primary indicating signals produced by the photo detectors 14 largely eliminates the noise problem.

The differential amplifier 42 also inverts the waveform; so that its output follows the waveform shown on line F of FIG. 5. The output signal of the differential amplifier is designated "X" in FIG. 3 because this is the signal which is shown entering the different readout versions shown in FIGS. 4, 6 and 7.

Figure 4:
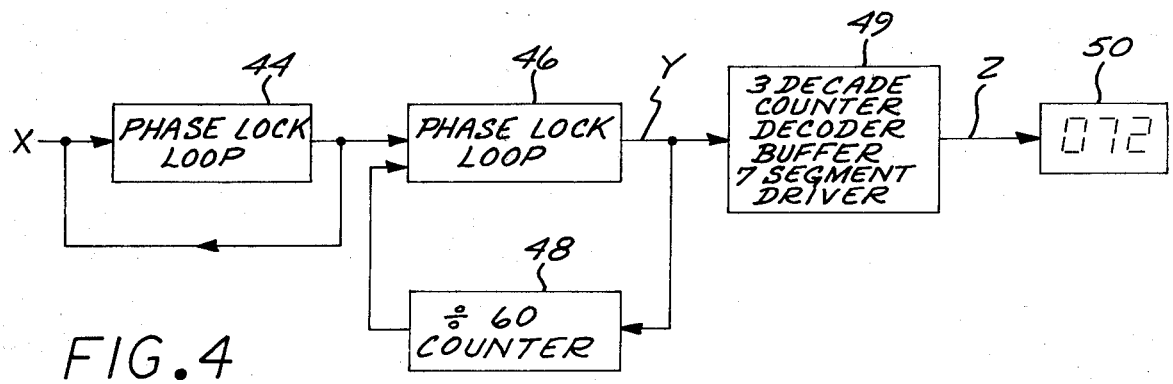
FIG. 4 is a schematic block diagram showing means for conversion of the sensor output into a digital readout of the heart pulse rate.

The preferred version is the full digital system shown in FIG. 4. In this system the signal "X" is an input to the phase lock loop 44. This phase lock loop tracks the recurrent incoming electrical pulse signal, and thus provides a further means of filtering out noise in the electrical signal. The phase lock loop 44 also squares the electrical pulse form, as shown on line G of FIG. 5. It further provides a 3-second averaging of the electrical pulse rate, which supplies a running average signal output not subject to transient pulse rate variations.

The electrical signal output from phase lock loop 44 is fed to a second phase lock loop 46, which is in a feedback loop with a divide-by-60 counter 48. Because the two inputs to phase lock loop 46, i.e., the original input and the feedback input, function as a phase detector, the voltage controlled oscillator included in phase lock loop 46 is caused to shift its frequency as required to provide an output signal which has 60 electrical pulses for each input pulse into the phase lock loop 46. This permits a "per second" counter to provide a "per minute" heart pulse rate readout.

The signal "Y" goes into a counter-driver 49 which provides the signal controlling the digital readout panel 50, which is shown in the figure displaying the numeral "72", thereby indicating a heart pulse rate of 72 pulses per minute. The driver 49 includes a clock oscillator which provides a "per second" pulse counter, which counts the pulse rate that was previously multiplied by 60. The driver, as indicated, is a 3 decade counter decoder buffer having a 7 segment driving signal output "Z" for actuating the digital readout device 50.

Figure 3:
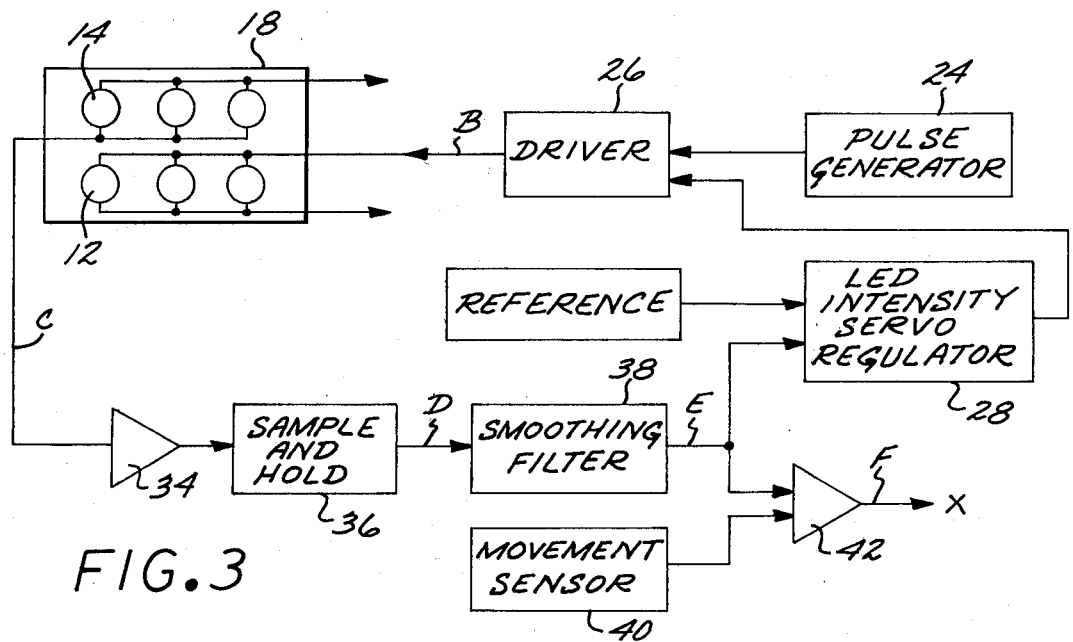
FIG. 3 is a schematic block diagram showing that portion of the circuitry of the heart rate monitor which constitutes the sensor electronics.

FIG. 6 shows the circuitry of an analog version of the heart rate monitor. The signal "X" from differential amplifier 42 of FIG. 3 is fed into a monostable multivibrator 52, which generates a fixed length pulse. This pulse is used to drive a tachometer generator 54, which generates an analog voltage proportional to frequency. This voltage is fed to a peak follower 56 to remove the normal saw-tooth envelope of the tachometer generator. The output "Z" of peak follower 56 is transmitted to a standard voltmeter 58, which displays the heart rate measurement.

FIG. 7 shows an alternative digital mechanization, wherein the voltage output "Z" is fed to an analogue-to-digital converter 60 which converts the voltage of a digital representation. After decoding by decoder-driver 62, this representation drives a 7-segment display 64.

It will be readily apparent that various versions other than the specific described embodiments are within the scope of my invention. The appended claims are intended to be interpreted as broadly as necessary to cover the several concepts of my invention and their logical ramifications.

What is claimed is:

1. A blood pulse sensor comprising:
   means for emitting an infra-red light toward a blood vessel, said light having a wavelength over 9,000 angstroms, thereby insuring its high absorption in the bloodstream constituents; and
   means for monitoring the relative absorption of said light in the bloodstream to indicate the timing of blood pulses.

2. A blood pulse sensor comprising:
   an infra-red light-emitting means located to direct light toward a localized area of a blood vessel; and
   an infra-red light-detecting means for receiving the back scatter of emitted infra-red light not absorbed by the blood as it passes through said area.

3. The blood pulse sensor of claim 2 wherein:
   the detecting means comprises a plurality of spaced infra-red light detecting devices which combine their light-induced signal output in an electrical output signal, thereby minimizing position sensitivity of the sensor with respect to the blood vessel location.

4. The blood pulse sensor of claim 3 wherein:
   the emitting means comprises a plurality of spaced infra-red light emitting devices, each of which is in a physically paired set with one of the light detecting devices;
   each paired emitting and detecting device being so located and having such angular dispersions of emitted and detected light ray patterns as to attain maximum illumination of the blood without saturating the detector device.

5. The blood pulse sensor of claim 4 which also comprises:
   means for compensating automatically for variations in flesh transparency to prevent over-stimulation or under-stimulation of the detecting means;
   said compensating means comprising a feedback circuit which increases the amplification at the emitting means as the average illumination level of the detecting means decreases, and decreases the amplification at the emitting means as the average illumination level of the detecting means increases.

6. The blood pulse sensor of claim 2 combined with:
   means responsive to the light-detecting means for developing electrical signals at intervals representing the blood pulse rate;
   means for providing an output signal which has sixty electrical pulses for each blood pulse signal; and
   means for counting the frequency per second of the pulses in said output signal to provide a blood pulse-per-minute readout.

7. The blood pulse sensor of claim 2 wherein the infra-red detecting means receives a substantially diminished light signal during the passage of the high pressure portion of the pulse.

8. A blood pulse sensor comprising:
   means for emitting an infra-red light toward a blood vessel, said light having a wavelength which has a high absorption in the bloodstream constituents;
   means for monitoring the relative absorption of said light in the bloodstream to indicate the timing of blood pulses;
   sensor means for developing an electrical signal responsive only to motion-induced noise, and
   means for algebraicly subtracting the electrical signal output of the sensor means from the electrical signal output of the monitoring means.

9. A blood pulse sensor comprising:
   means for emitting an infra-red light toward a blood vessel, said light having a wavelength which has a high absorption in the bloodstream constituents;
   means for monitoring the relative absorption of said light in the bloodstream to indicate the timing of blood pulses; and
   means for controlling the light-emitting means to cause light emission pulses which are drawing electrical power only a small fraction of the time to provide a periodic sampling by the monitoring means.

10. The blood pulse sensor of claim 9 which also comprises:
    means for compensating automatically for variations in flesh transparency to prevent over-stimulation or under stimulation of the detceting means;
    said compensating means comprising a feedback circuit which increases the amplification at the emitting means as the average illumination level of the detecting means decreases, and decreases the amplification at the emitting means as the average illumination level of the detecting means increases.

11. A blood pulse sensor comprising:
    a plurality of spaced light-emitting devices located to direct light toward a localized area of a blood vessel;
    a plurality of spaced light-detecting devices for sensing light from the emitting devices after it has illuminated the blood vessel;
    each of the light-detecting devices being in a physically paired set with one of the light-emitting devices;
    each paired emitting and detecting device having an angular ray emission from the emitting device and an angular ray detection by the detecting device which overlap optically at a predetermined optimal blood vessel illumination depth.

12. The blood pulse sensor of claim 11 wherein: the spacing between the emitting and detecting device of each paired set is in the approximate range of 0.25 to 0.35 inch; and
    the light emission angle is relatively narrow and the light detection angle is relatively broad.

13. The blood pulse sensor of claim 12 wherein:
    the light emission angle is in the neighborhood of 10° and the light detection angle is in the neighborhood of 90°.

14. A blood pulse sensor comprising:
    a light emitting means located to direct light toward a localized area of a blood vessel;

a light-detecting means for sensing light from the emitting means after it has illuminated the blood vessel; and means for compensating automatically for variations in flesh transparency to prevent over-stimulation or understimulation of the light-detecting means.

15. The blood pulse sensor of claim 14 wherein:

the compensating means comprises a feedback circuit which increases the amplification at the emitting means as the average illumination level of the detecting means decreases, and decreases the amplification at the emitting means as the average illumination level of the detecting means increases.

16. The blood pulse sensor of claim 14 which also comprises:

means for controlling the light-emitting means to cause light emission pulses which are drawing electrical power only a small fraction of the time to provide a periodic sampling by the detecting means.

17. A blood pulse sensor comprising:

a light-emitting means located to direct light toward a localized area of a blood vessel;

a light-detecting means for sensing light from the emitting means after it has illuminated the blood vessel; and means for controlling the light-emitting means to cause light emission pulses which are drawing electrical power only a small fraction of the time to provide a periodic sampling by the detecting means.

18. The blood pulse sensor of claim 17 wherein the controlling means causes light emission pulses having: (a) a pulse frequency as low as practical consistent with the frequency of the heart rate being measured, and (b) a pulse width as narrow as practical consistent with the response characteristics of the detecting means.

19. The blood pulse sensor of claim 18 wherein the light emission pulses have a pulse frequency in the neighborhood of 20 Hertz and a pulse width in the neighborhood of 60 microseconds.

20. A blood pulse sensor comprising:

means for emitting an infra-red light toward a blood vessel, said light having a wavelength which has a high absorption in the bloodstream constituents;

means for monitoring the relative absorption of said light in the bloodstream to indicate the timing of blood pulses; and means for compensating automatically for variations in flesh transparency to prevent over-stimulation or understimulation of the monitoring means.

21. The blood pulse sensor of claim 5 wherein:

the compensating means comprises a feedback circuit which increases the amplification at the emitting means as the average illumination level of the monitoring means decreases, and decreases the amplification at the emitting means as the average illumination level of the monitoring means increases.

* * * * *

UNITED STATES PATENT OFFICE
CERTIFICATE OF CORRECTION

Patent No. 4,063,551　　　　Dated December 20, 1977

Inventor(s) James Stevens Sweeney

It is certified that error appears in the above-identified patent and that said Letters Patent are hereby corrected as shown below:

Claim 21, line 1, "5" should read -- 20 --.

Signed and Sealed this

Second Day of May 1978

[SEAL]

Attest:

RUTH C. MASON　　　　LUTRELLE F. PARKER
Attesting Officer　　　　Acting Commissioner of Patents and Trademarks